US007132108B1

United States Patent
Yang et al.

(10) Patent No.: US 7,132,108 B1
(45) Date of Patent: Nov. 7, 2006

(54) **BIODEGRADABLE AND BIOCOMPATIBLE POLYMERIC MICROSPHERES ENCAPSULATING *SALMONELLA ENTERITIDIS* BACTERIA**

(75) Inventors: Yi-Yan Yang, Singapore (SG); Jimmy Kwang, Singapore (SG); Xueqin Chen, Singapore (SG); Tai-Shung Chung, Singapore (SG); Wei Liu, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 0 days.

(21) Appl. No.: 09/958,210

(22) PCT Filed: Feb. 8, 2000

(86) PCT No.: PCT/SG00/00017

§ 371 (c)(1),
(2), (4) Date: Oct. 5, 2001

(87) PCT Pub. No.: WO01/58466

PCT Pub. Date: Aug. 16, 2001

(51) Int. Cl.
*A61K 39/112* (2006.01)
*A61K 9/52* (2006.01)
*A61K 9/32* (2006.01)
*C12P 1/00* (2006.01)

(52) U.S. Cl. .................. 424/258.1; 424/457; 424/482; 435/41

(58) Field of Classification Search ............. 424/258.1, 424/278.1, 282.1, 450, 457, 462, 470, 482, 424/489, 262
See application file for complete search history.

(56) References Cited

U.S. PATENT DOCUMENTS 6,309,669 B1 * 10/2001 Setterstrom et al. ........ 424/486

FOREIGN PATENT DOCUMENTS

| EP | 0 300 102 A1 | 1/1989 |
|---|---|---|
| WO | WO 99/43349 A1 | 9/1999 |

OTHER PUBLICATIONS

Hazrati et al, Proceedings Intern. Symp. Control Rel. Bioact. Material., 20 1993.*
Hazrati et al, Proceed Intern. Symp. Control Rel. Bioact. Mater., 20(1993).*
Hazrati et al, Proceed Intern. Symp. Control Rel. Bioact. Mater., 20(1993), Controlled Release Society, Inc.*
Hazrati et al (Proceed Intern. Symp. Control Rel. Bioact. Mater., 20(1993).*
Liu et al (Conf. Res. Workers Anim. Dis. (80 Meet. 13P, Nov. 1999, Chicago, Illinois).*
Chart et al (FEMS Microbiol. Letter, Dec. 1:68(3):345-50) (Abstract only).*
Yan C, et al., "Characterization and morphological analysis of protein-loaded poly (lactide-co-glycolide) microparticles prepared by water-in-oil-in-water emulsion technique" Journal of Controlled Release, vol. 32, 1994, pp. 231-241. Elsevier Science Publishers B.V., Amsterdam.

* cited by examiner

*Primary Examiner*—Nita Minnifield
*Assistant Examiner*—Vanessa L. Ford
(74) *Attorney, Agent, or Firm*—Rothwell, Figg, Ernst & Manbeck

(57) ABSTRACT

Biodegradable and biocompatible polymeric microspheres encapsulating *Salmonella enteritidis* are administered to chickens to provide the chickens with sustained protection against *S. enteritidis* infections.

3 Claims, 5 Drawing Sheets

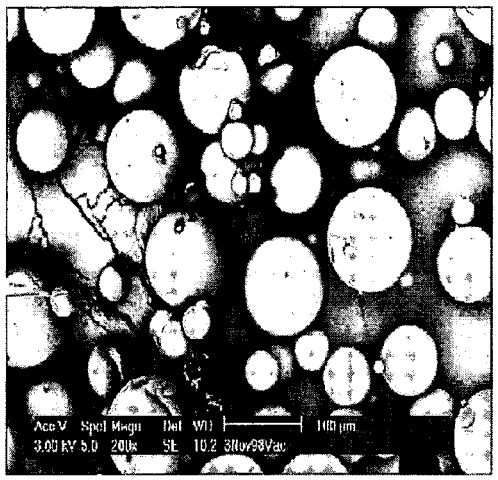 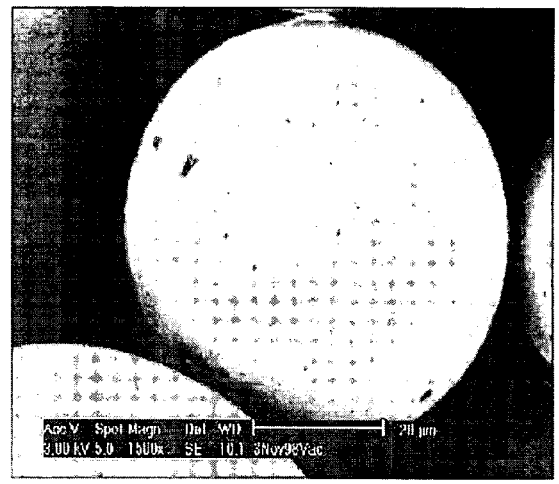
PLGA 65:35, 200 X, scale bar: 100 μm    PLGA 65:35, 1500 X scale bar 20 μm
Figure 1A
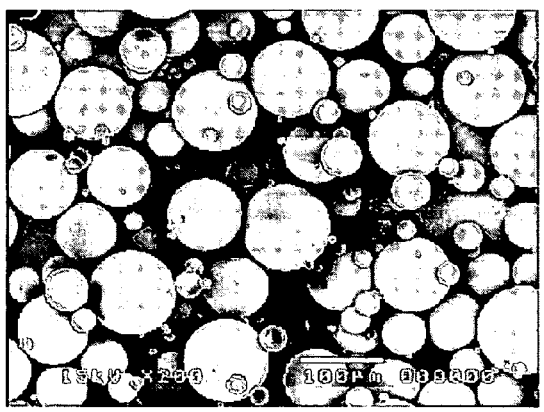 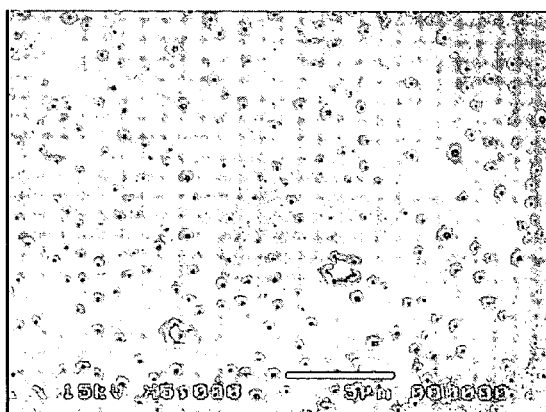
PLGA 50;50, 200 X, scale bar: 100 μm    PLGA 50:50, 5000 X, scale bar: 5 μm
Figure 1B PLGA 50:50, 5000X, scale bar: 5 μm

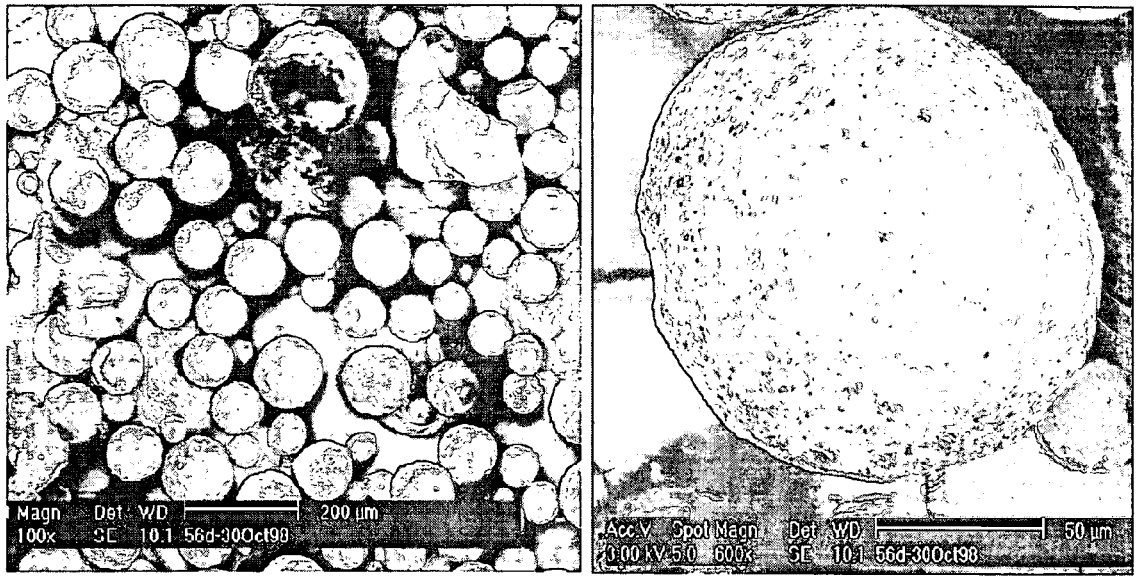
100X, scale bar: 200 μm  600X, scale bar: 50 μm
Figure 3A: PLGA 65:35, released for 56 days
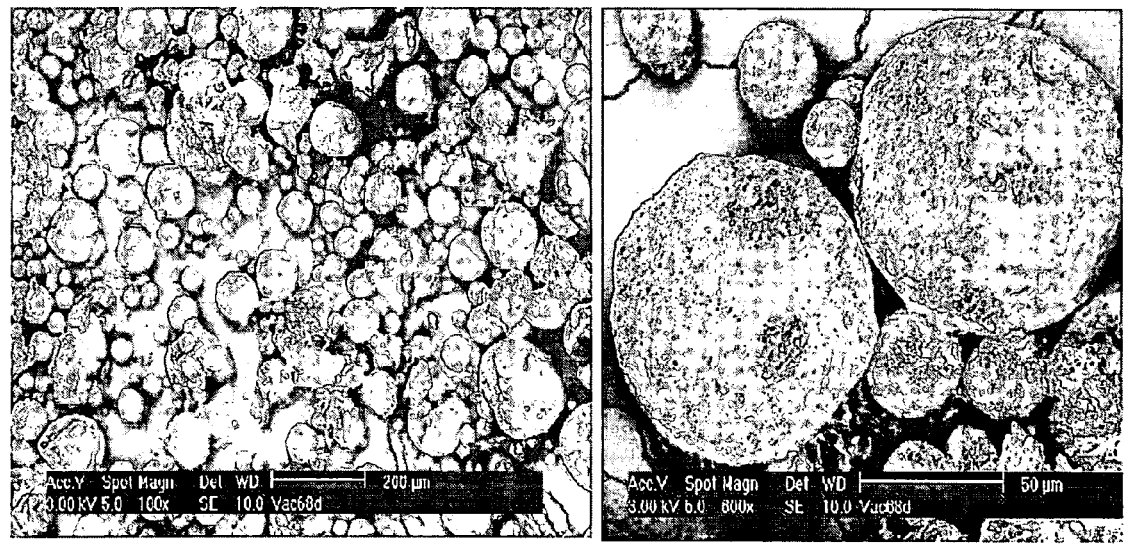
100X, scale bar: 200 μm  500X, scale bar: 50 μm
Figure 3B: PLGA 65:35, released for 68 days

US 7,132,108 B1

BIODEGRADABLE AND BIOCOMPATIBLE POLYMERIC MICROSPHERES ENCAPSULATING *SALMONELLA ENTERITIDIS* BACTERIA

BACKGROUND OF THE INVENTION

1. Field of the Invention

This invention relates to compositions and methods for providing chicken with sustained protection from infection with *Salmonella enteritidis*. More specifically, this invention relates to biodegradable and biocompatible polymeric microspheres encapsulating *S. enteritidis* which can be administered to chickens to protect them from *S. enteritidis* infections.

2. Background Art

*Salmonella enteritidis*, an agent which causes salmonellosis in poultry, can be transmitted vertically from laying hens to eggs. Consumption of eggs or meat contaminated with the organism can lead to food poisoning in humans. This is a worldwide problem in public health; in the U.S. alone, more than a million cases of salmonellosis are reported annually. Outbreaks in the elderly and in young children can be especially dangerous, resulting in severe gastroenteritis and possibly fatal septicemia.

In view of the large number of cases of *Salmonella enteritidis* cases reported each year, there is an obvious need for a reliable method for controlling the spread of *Salmonella* intestinal pathogens in poultry and for preventing the transmission of the pathogens into their eggs. Avirulent and killed injectable *S. enteritidis* vaccines have been developed and are useful. These vaccination processes, however, are known to cause a large amount of stress to the chicken as multiple vaccinations are required.

There thus is a significant need for a method by which poultry can be immunized against *S. enteritidis* in a simple, single dose, efficient, and cost-effective manner.

SUMMARY OF THE INVENTION

In accordance with the present invention, there are provided long term release, biocompatible and biodegradable, porous, polymeric microcapsules comprising whole killed *S. enteritidis* bacteria. Upon administration, the *S. enteritidis* is released in a biphasic pattern, wherein about 20% to about 50% of the *S. enteritidis* is released in an initial burst over the period of about 7 to 15 days, followed by the release of the remaining *S. enteritidis* in a steady and sustained manner over a period of about 70 to about 100 days. The microcapsules can be made by a (water-in-oil)-in-water emulsion process.

BRIEF DESCRIPTION OF THE DRAWINGS

FIGS. 1A and 1B show the size distribution and morphology of *S. enteritidis*-loaded microspheres formed using PLGA 65:35 and PLGA 50:50, respectively.

FIGS. 3A and 3B show the size distribution and morphology of *S. enteritidis*-loaded microspheres formed using PLGA 65:35 after release.

DETAILED DESCRIPTION OF THE INVENTION

Figure 2:
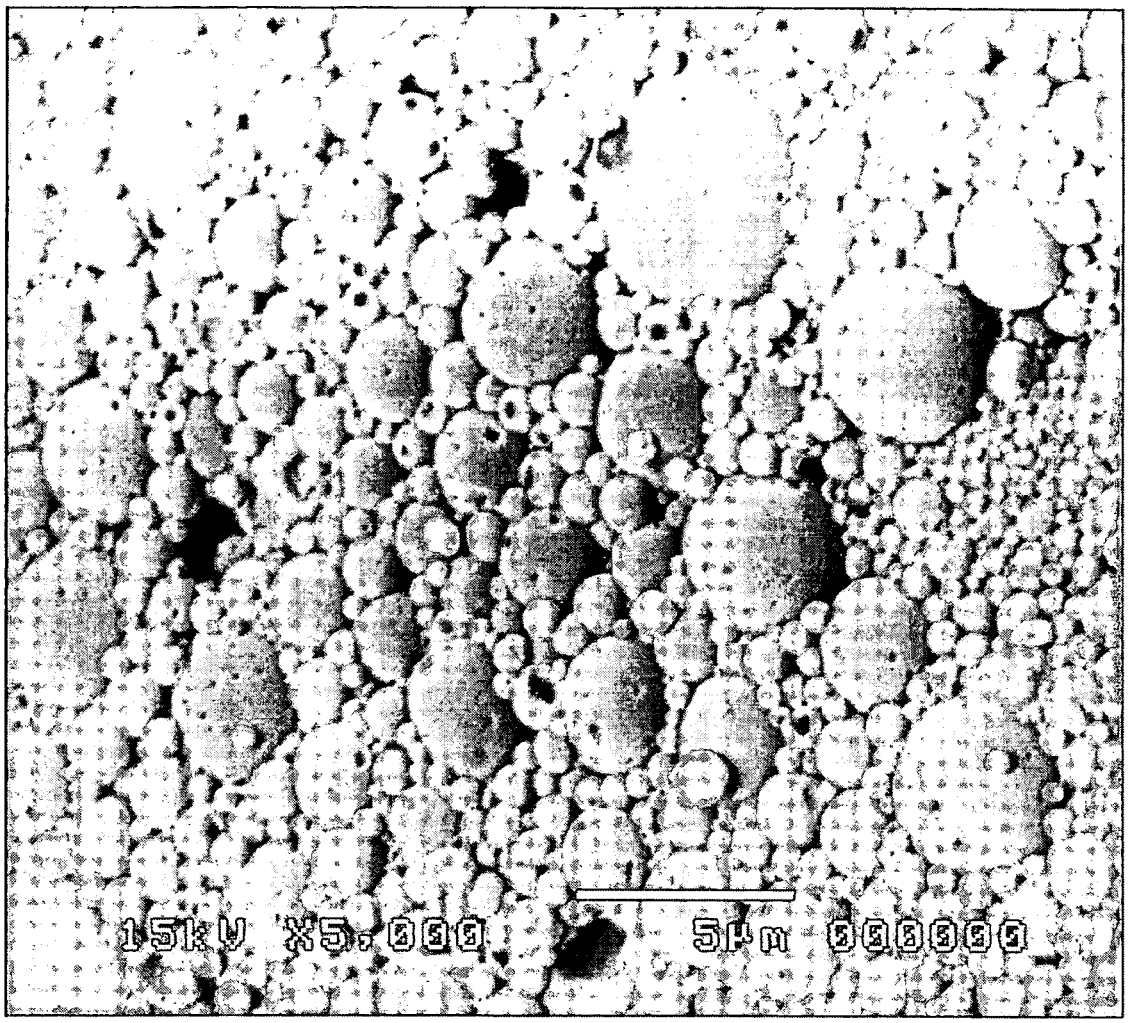
FIG. 2 shows the size distribution and morphology of *S. enteritidis*-loaded microspheres formed using PLGA 50:50.

Microencapsulation is a process whereby very small droplets or particles of an active or otherwise desirable substance are distributed uniformly in a polymer matrix which is essentially inert and serves to isolate or protect the desirable substance. The desirable material is released from the polymeric matrix through erosion, permeation or rupture of the matrix. Variation in the size or material of the matrix and in the method by which the microcapsules are made can be utilized to control the rate or timing of the release of the core material. In the following description, the compositions of the present invention are described as microspheres. As used herein, this term encompasses microcapsules and microparticles. The term also encompasses "sub micron" spheres, i.e., spheres between about 0.1 µm and 10 µm in diameter.

In accordance with the present invention, it now has been discovered that microspheres containing whole, killed *S. enteritidis* can be administered to poultry to protect the poultry from *S. enteritidis* infection. One dose of the vaccine of this invention has been found to provide poultry with protection from *S. enteritidis* infection as soon as 3–4 weeks post-administration and lasting for a period of at least six months.

The microspheres of the present invention are characterized as having a biphasic release pattern. Specifically, the microspheres provide a high initial release rate of about 20% to about 50% of the total *S. enteritidis* in the microspheres for a period of about 7 to about 15 days, preferably about 7–10 days followed by a lower, steady rate of release of the remaining *S. enteritidis* which occurs over a longer period of time, as described in detail below.

A preferred method for forming the microspheres of the present invention is to dissolve a polymer of choice in a solvent or solvents. More specifically, the preferred method uses a technique known as the double emulsion method (also called the complex emulsion method). In the double emulsion method, an aqueous solution of the *S. enteritidis* bacteria is emulsified with a larger quantity of a non-aqueous solution of a selected polymer. The emulsion can be made by sonication or by homogenization. A preferred solvent is methylene chloride. Other suitable solvents include ethyl acetate, acetone, tetrahydrofuran and chloroform. The volume:volume ratio of aqueous solution to non-aqueous solution generally is within the range of 1:80 to about 1:12, and preferably is within the range of about 1:40 to about 1:12.

Choice and amount of solvent can affect the size and release profile of the resulting microspheres. The amount of $CH_2Cl_2$ or other solvent affects the viscosity of the polymer solution. Using a relatively low amount of $CH_2Cl_2$ will provide a more viscous polymer solution, ultimately resulting in bigger microspheres and, eventually, a longer overall time period of *S. enteritidis* release. Increasing the amount of $CH_2Cl_2$ relative to the amount of polymer used will result in the ultimate formation of more porous (and, hence, faster releasing) microspheres.

Desirably, the concentration of polymer in solution is within the range of about 12 to about 150 mg/ml and preferably is within the range of about 30 to about 80 mg/ml. These suggested concentrations can be modified, as suggested above, if it is desired to significantly change the *S.*

*enteritidis* release profile. Also desirably, the aqueous solution of *S. enteritidis* is within the range of about 20 mg/ml to about 600 mg/ml and preferably is within the range of about 30 to about 400 mg/ml. The weight:weight ratio of polymer to *S. enteritidis* affects the release rate of the *S. enteritidis*. The release rate increases slightly as the ratio decreases. The ratio of the range of polymer weight to *S. enteritidis* weight is within 1.5:1 to 40:1 and preferably is within the range of about 4:1 to about 40:1.

The resulting emulsion then is emulsified further by mixing (microspheres) or by either sonication or homogenization (sub-micron spheres) in a still larger quantity of an aqueous solution, forming a (water-in-oil)-in-water double emulsion. A preferred solution for forming the second emulsion is phosphate buffered saline (PBS), which further can comprise an emulsifier. Suitable emulsifiers include polyvinyl alcohol (PVA), span 80 and Tween 80. Suitable amounts of emulsifier generally are within the range of about 0.01% to about 5% by weight; a preferred amount of PVA is about 0.05% by weight for microspheres and about 0.5% by weight for sub-micron spheres. The higher the emulsifier concentration, the smaller the sphere size, which will result in a faster release profile of the *S. enteritidis*.

Changing the volume ratio of first emulsion to second emulsion can affect the removal rate of the solvent. The removal rate of the solvent is increased as this ratio decreases, resulting in a denser skin layer of microsphere and further in a slow release of *S. enteritidis*. The volume ratio of first emulsion to second emulsion is within the range of about 1:500 to about 1:1.5. Preferably the ratio is within the range of about 1:50 to about 1:1.5.

The polymer solvent then is allowed to be removed by evaporation and/or extraction, hardening the polymer and encapsulating the inner water droplets which contain the bacteria into small microspheres, generally about 0.1 to about 400 μm median diameter, preferably about 5 to about 120 μm median diameter. When hardening is complete, the microspheres are filtered (microspheres) or centrifuged (sub-micron spheres), washed and dried. Filtering can be with a 0.02 μm to a 20 μm mesh, preferably a 5 μm mesh. Washing can be carried out using about 15 ml to about 5000 ml water, typically with about 100 ml to about 500 ml phosphate buffered saline (PBS). Drying can be accomplished using such methods as vacuum drying, lyophilization and fluidized bed drying in accordance with conventional techniques.

Desirably, the microspheres produced in accordance with this invention comprise about 25 μg to about 400 μg *S. enteritidis* per mg of spheres. Typically, the microspheres are administered such that the animal will receive a total dose of the killed *S. enteritidis* of at least about 0.15 mg. Preferably, a total dose of about 0.15 mg to about 15 mg is administered per chicken.

The release of the *S. enteritidis* can occur by two different mechanisms. The *S. enteritidis* can be released by diffusion through aqueous-filled channels in the polymeric matrix which are the result of voids or pores created by the internal aqueous phase or by solvent removal during the formation of the microspheres. The porosity of the microspheres result in a high initial burst of *S. enteritidis* release upon administration of the microspheres, as *S. enteritidis* at or near the surfaces of the pores of the microspheres dissolves in body fluids which enter the pores and is carried away from the spheres. In accordance with the present invention, approximately 20% to about 50% of the total encapsulated *S. enteritidis* is released in the initial burst, which typically takes place over a period of about 7 to about 15 days. By achieving such an initial release rate, poultry administered the microspheres show an obvious antibody response only 3–4 weeks post-injection. This is an advantage over immunization methods known in the art which have not resulted in a clear antibody response until 50 days post-immunization.

A second mechanism of release is the release of *S. enteritidis* due to degradation of the polymer. This follows the initial burst release of *S. enteritidis*, and results in the remaining *S. enteritidis* in the microspheres being released more gradually. Typically, the remaining *S. enteritidis* is released steadily over a period of at least about 10 to about 15 weeks. The rate of degradation can be controlled by changing polymer properties that influence the rate of hydration of the polymer. These properties include, for example, the choice of monomers used, the ratio of different monomers which comprise the polymer, and the molecular weight of the polymers. These properties can affect the hydrophilicity and crystallinity of the polymer, which in turn control the rate of hydration of the polymer. Hydrophilic excipients, such as carbohydrates, surfactants, polyethylene glycol (PEG) and low molecular weight polyesters also can be incorporated in the polymer to increase hydration and alter the rate of erosion of the polymer.

Polymers useful in the present invention include poly (lactide) (PLA), polyglycolide (PLG), poly(lactide-co-glycolide) copolymers (PLGA), polyethylene glycol (PEG), polyorthoesters, polyanhydrides and polyphosphoesters. Preferred polymers are poly(lactide-co-glycolide) copolymers. Although the polymer can be all poly(lactide) or all polyglycolide, a blend of the two polymers (PLGA copolymers) preferably is used, and that copolymer preferably has a composition which is within the range of about 65:35 to about 50:50. Suitable molecular weights of the polymers are within the range of about 10,000 to about 110,000. Desirably, the molecular weight is about 40,000 to about 75,000 for 50:50 compositions and about 10,000 to about 75,000 for 65:35 compositions.

By varying the properties of the polymer, i.e., its composition, molecular weight, or its nature, one can affect the release rate, the proportion of bacteria released by diffusion vs. degradation, and the overall release period. For example, varying the molecular weight of the PLGA or the content of lactide in the polymer affects the rate at which the microspheres will degrade in body fluids. Increasing the glycolide content of a poly(lactide-co-glycolide) polymer and decreasing the molecular weight of the polymer can enhance the hydrolysis of the polymer and so provide increased *S. enteritidis* release from polymer erosion. Using higher molecular weights of PLGA, e.g., in the range of about 75,000 to about 110,000, or using a content of lactide to glycolide of at least about 75:25, the period of *S. enteritidis* release following the initial burst can be extended. However, a larger volume of internal aqueous solution desirably is used to achieve more porous microspheres which can still result in a desirable initial release even with PLGA polymers comprising a high content of polylactide to polyglycolide. Also, the degradation rate of the microspheres can be adjusted by using a combination of two different kinds of polymers. For example, the degradation rate of polycaprolactone (PCL) is much slower than that of PLGA; the degradation rate of PEG is much faster. Microspheres fabricated with a blend of PEG and PLGA will have a much faster degradation rate and a faster rate of total release of *S. enteritidis*. PEG has little effect on the initial burst of release; the release of *S. enteritidis* in the initial burst is controlled by the porosity of the microspheres.

Polyorthoesters and polyanhydrides also can be used to deliver *S. enteritidis* in a biphasic release pattern as described above for PLGA. Persons of skill in the art can design the composition of the polymeric matrix to have a specific desired release profile given the guidance provided herein.

The pH of the formulations of this invention is generally in the range of about 5 to about 8.

The formulations of the present invention can comprise other components in addition to the *S. enteritidis*, provided that any such additional component does not interfere with the *S. enteritidis* or its release from the microspheres and is provided in an amount suitable for safe and effective pharmaceutical administration. Such additional components can include adjuvants, nutrients, drugs, peptides, and immunomodulators. Useful adjuvants include aluminum hydroxide, latex particles or liposomes, which adsorb antigen and enhance immune responses. Other useful adjuvants can include saponin and mineral oil.

Peptides of interest include muramyl dipeptide (MDP), which enhances antibody production and stimulates and activates macrophages. Trehalose dimycolate also can be included to stimulate macrophages.

Immunomodulators which can be provided in the compositions of the present invention include cytokines, which have a complex activity to stimulate phagocytosis by macrophages or neutrophils, increase the activity of natural killer cells and increase production of other cytokines. Another useful immunomodulator is tumor necrosis factor (TNF). Certain complex carbohydrates, such as Zymogen, glucan, dextran sulfate and lectinans, also can be included to serve as immunostimulators and to activate macrophages.

To administer the microspheres of the present invention, a suitable amount of the microspheres can be suspended in a PBS solution and the resulting suspension is administered by injection or orally to poultry. A suitable dose comprises about 0.15 mg to about 15 mg of the killed, whole *S. enteritidis*. The injections are administered intramuscularly or subcutaneously. Oral administration can be by dropper or by mixing the suspension of microspheres in poultry feed.

As indicated above, it has been found that a single dose comprising an amount of *S. enteritidis* within the ranges set forth above is sufficient to provide at least about 6 months of protection from infection by *S. enteritidis*. Protection is effective within about 3–4 weeks of immunization.

EXAMPLES

Example 1

Preparation of PLGA 65:35 Microspheres with 5% (wt) of Loading of *S. enteritidis*

Six hundred mg of polymer PLGA 65:35 were as dissolved in 12 ml of $CH_2Cl_2$. To this solution was added 0.5 ml of a *S. enteritidis* aqueous suspension (72 mg/ml, internal aqueous phase) to produce the primary emulsion by sonication. The resulting emulsion was injected with stirring into 250 ml of phosphate buffered saline (PBS) containing 0.05% wt of polyvinyl alcohol (PVA) as an emulsifier at 15° C. to produce a double emulsion. Then 640 ml of PBS containing 0.05% wt of PVA was added to this solution for 4 hours in order to extract $CH_2Cl_2$ into the external phase. The resulting *S. enteritidis*-containing microspheres were filtered, washed with PBS, and vacuum-dried. The microspheres ranged in size from 0.5 to 120 µm, which were suitable for injection dosage. FIG. 1A shows the size distribution and morphology of the microspheres. It is clear that *S. enteritidis*-containing microspheres produced had a porous structure. The porous structure will allow a high initial release of *S. enteritidis* once the microspheres are administered, which, in turn, will result in a high response of antibody.

Example 2

PLGA 65:35 Microspheres with 10% (wt) loading of *S. enteritidis*

600 mg of polymer PLGA 65:35 were dissolved in 12 ml of $CH_2Cl_2$. To this solution was added 0.5 ml of a suspension of *S. enteritidis* in water (144 mg/ml) to produce the primary emulsion by sonication. The other steps were the same as in Example 1, above. The resultant microspheres ranged in size from 0.5 to 120 µm, suitable for injection dosage.

Example 3

PLGA 50:50 Microspheres with 5% (wt) loading of *S. enteritidis*

600 mg of PLGA 50:50 were dissolved in 12 ml of $CH_2Cl_2$. To this solution was added 0.5 ml of a suspension of *S. enteritidis* in water (72 mg/ml) to produce the primary emulsion by sonication. The remaining steps were the same as in Example 1, above. The majority of the microspheres produced ranged in size from 40 to 80 µm, suitable for injection. The size distribution and morphology of the microspheres are demonstrated in FIG. 1B. As in Example 1, the microspheres had a porous morphology.

Example 4

PLGA 50:50 Microspheres with 10% (wt) or loading of *S. enteritidis*

600 mg of PLGA 50:50 were dissolved in 12 ml of $CH_2Cl_2$. To this solution was added 0.5 ml of a suspension of *S. enteritidis* in water (144 mg/ml) to produce the primary emulsion by sonication. The remaining steps were the same as in Example 1, above. The majority of the microspheres had a size in the range of about 40 to about 80 µm, suitable for injection dosage.

Example 5

PLGA 50:50 Submicrospheres with 10% (wt) loading of *S. enteritidis*

400 mg of PLGA 50:50 were dissolved in 4 ml of $CH_2Cl_2$. To this solution was added 0.1 ml of a suspension of *S. enteritidis* in water (400 mg/ml) to produce the primary emulsion by sonication. The emulsion was mixed with 6 ml of PBS containing 0.5% PVA to produce a double emulsion by sonication. The double emulsion was poured into 150 ml of PBS containing 0.05% PVA with stirring. The 250 ml of PBS containing 0.05% wt PVA were added to the solution for 2 hours in order to extract $CH_2Cl_2$ into the external phase. The resulting *S. enteritidis*-containing microspheres were centrifuged, washed with PBS and vacuum dried. The resulting microspheres ranged in size from about 0.1 to about 10 µm, which are easily taken up by Peyer's patches in the intestine and are suitable for oral administration. The distribution and morphology of the microspheres is shown in FIG. 2.

Example 6

Figure 4:
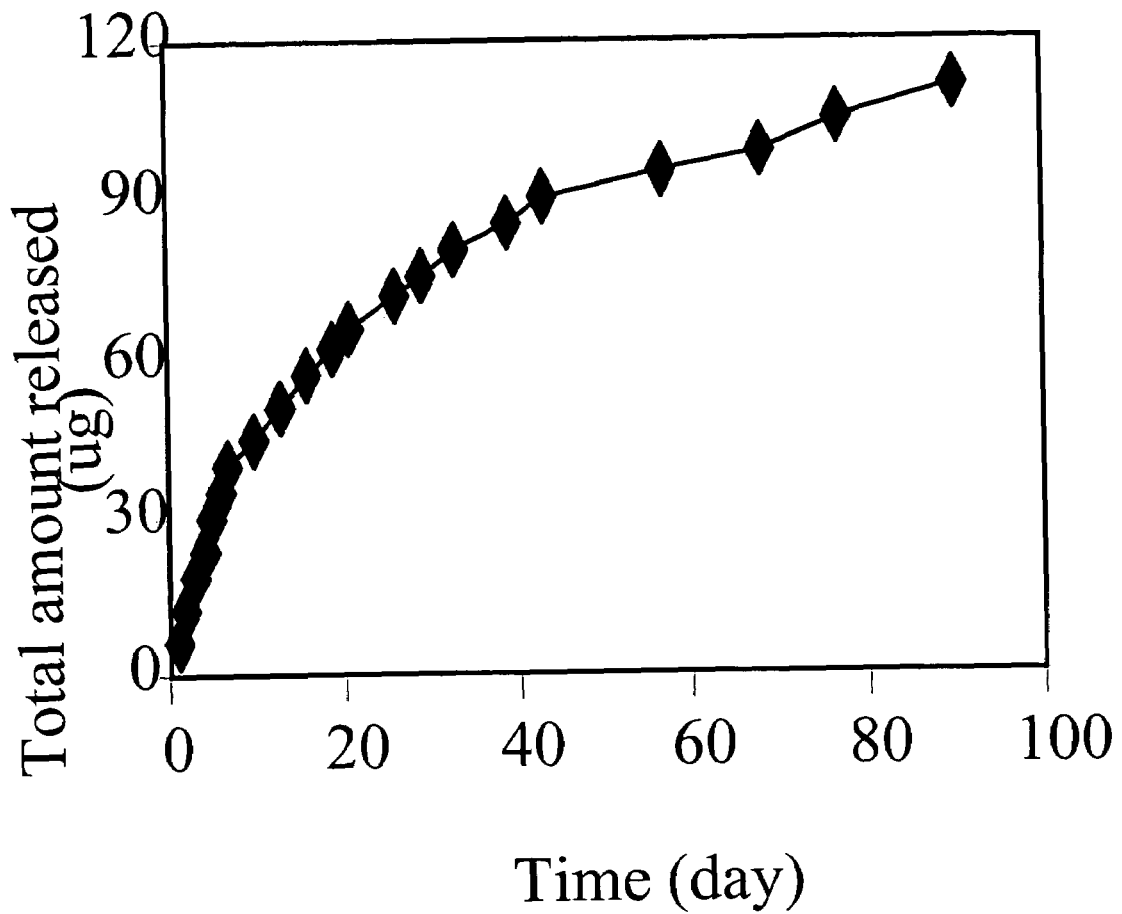
FIG. 4 shows the in vitro release profile of *S. enteritidis*-loaded microspheres (calculated in 3 mg of the microspheres) formed using PLGA 65:35 after release.

In Vitro Release Kinetics 30 mg of the microspheres produced in Example 1 were suspended in 1 ml of PBS pH 7.4 at 37° C. The supernatant was removed using a syringe and replaced with fresh PBS at regular intervals. The content of antigen in the supernatant was measured using an ELISA. The results showed that the duration of *S. enteritidis* release by the microspheres was more than two months and there was a high initial release of 110 µg/5 mg microspheres over 10 days. This initial release was followed by more than three months of steady release of the remaining *S. enteritidis*. FIG. 3 shows the change in size distribution and morphology after release. FIG. 4 shows the in vitro release profile (calculated in 3 mg of the microspheres) of the specific microspheres composed of PLGA 65:35 produced in Example 1.

Example 7

Chicken Test 1

Figure 5:
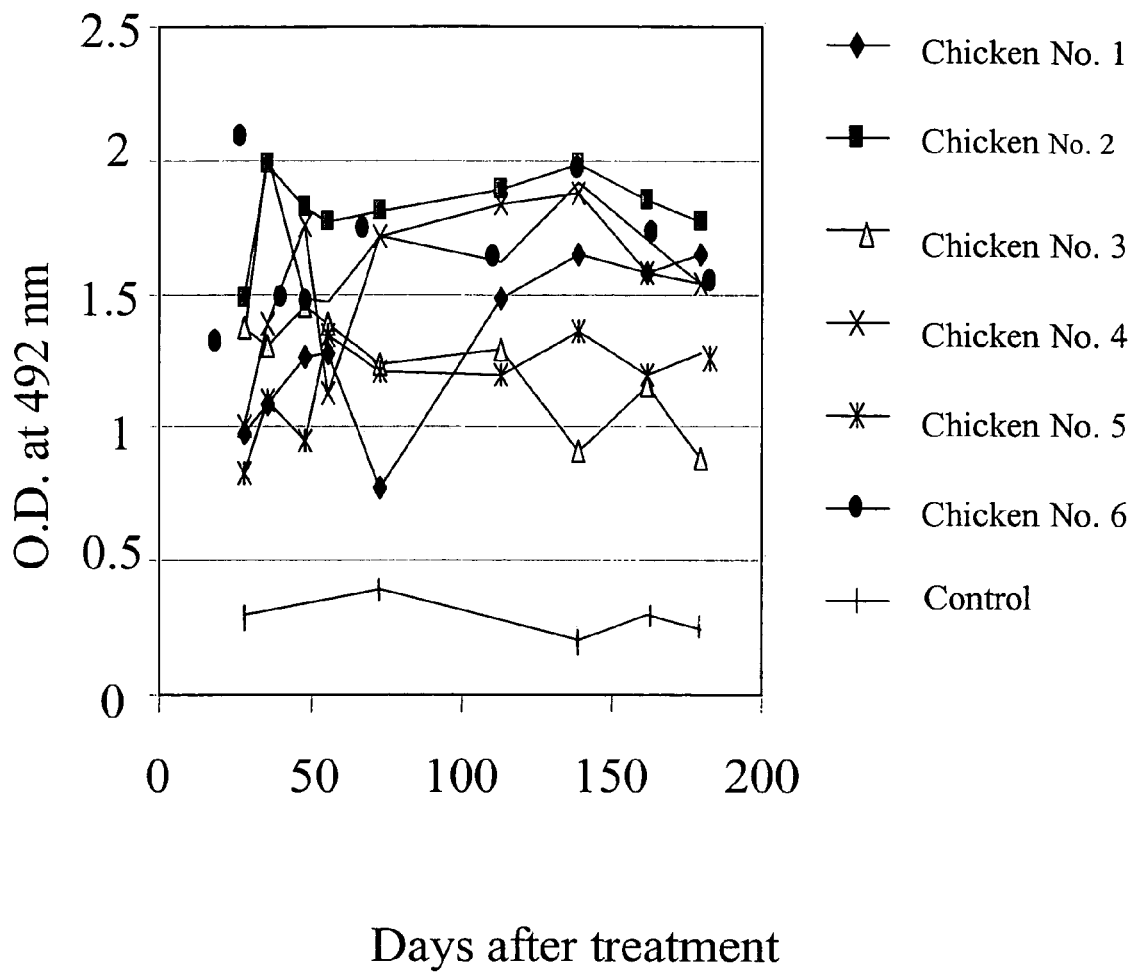
FIG. 5 shows antibody response in chicken treated with the *S. enteritidis*-loaded microspheres formed using PLGA 65:35.

5 mg of the *S. enteritidis*-loaded microspheres produced in Example 1 were suspended in 150 µl of PBS, then injected into 6 two-day old chicks. Blood samples of the treated chicks were taken at one or four weeks post-injection. FIG. 5 shows the antibody response of the chicks post-treatment with the *S. enteritidis*-loaded microspheres. The microspheres successfully induced an antibody response in the chicks within four weeks which was maintained for six months.

Example 8

Chicken test 2

The following formulations were prepared and administered:

1. 5 mg. of *S. enteritidis*-loaded microspheres made in accordance with Example 2 were suspended in 150 µl of distilled water and injected intramuscularly in each of six 7-day old chicks.
2. 5 mg. of *S. enteritidis*-loaded microspheres made in accordance with Example 4 were suspended in 150 µl of distilled water and injected intramuscularly in each of six 14-day old chicks.
3. 9 mg of *S. enteritidis*-loaded microspheres made in accordance with Example 5 was administered orally by dropper to six 14-day old chicks.
4. A fourth group of six 14-day old chicks was used as a control group and did not receive any *S. enteritidis*-loaded microspheres.

Seven day old chicks were used in (1) above to investigate whether chick age had any effect on immunization.

A month after the *S. enteritidis* administration, the chicks in each of the three treatment groups, as well as the control group, were challenged with $5 \times 10^7$ live *S. enteritidis*. All of the chicks in group 4 became sick and showed clinical signs such as manifest somnolescence, weakness, loss of appetite and adherence of chalky white material to the vent. All of the chicks treated with the *S. enteritidis* polymeric microspheres, however, showed no symptoms of disease. The results of the challenge are presented in Table 1 below. From these results, it is clear that the *S. enteritidis* microspheres of the present invention protect chicks from live *S. enteritidis* challenge.

TABLE 1

Challenge Results of Chickens Following Treatment with the *S. enteritidis* Microspheres

| Experimental Group | Chicken Number | Age (days) | Sick |
|---|---|---|---|
| Group 1 | 6 | 7 | 0/6 |
| Group 2 | 6 | 14 | 0/6 |
| Group 3 | 6 | 14 | 0/6 |
| Group 4 | 6 | 14 | 6/6 |

The invention claimed is:

1. A method for immunizing poultry from infection from *Salmonella enteritidis* which comprises administering to poultry a total dose of killed *S. enteritidis* of about 0.15 mg to about 15 mg, said dose administered as a single dose of a suspension of microspheres comprising killed *S. enteritidis* encapsulated in a porous polymeric shell comprising poly (lactide-coglycolide) copolymers; wherein the *S. enteritidis* is released from the microspheres in a biphasic pattern upon administration wherein about 20% to about 50% of the encapsulated *S. enteritidis* is released in a first phase in an initial burst within the first 7 to about 15 days of the administration of the suspension and the remainder of the *S. enteritidis* is released in a second phase over a period of about 10 to about 15 weeks.

2. The method of claim 1, wherein the poultry have protection from infection within about 3–4 weeks of the administration of the microspheres.

3. The method of claim 2, wherein protection from infection is effective for at least about 6 months.

* * * * *